(12) United States Patent
Parker et al.

(10) Patent No.: US 8,892,201 B2
(45) Date of Patent: Nov. 18, 2014

(54) PHARMACEUTICAL AGENT DELIVERY IN A STIMULATING MEDICAL DEVICE

(71) Applicants: John L. Parker, Reseville (AU); James F. Patrick, Roseville (AU); Paul Carter, West Pennant Hills (AU)

(72) Inventors: John L. Parker, Reseville (AU); James F. Patrick, Roseville (AU); Paul Carter, West Pennant Hills (AU)

(73) Assignee: Cochlear Limited, Macquarie University, NSW (AU)

( * ) Notice: Subject to any disclaimer, the term of this patent is extended or adjusted under 35 U.S.C. 154(b) by 0 days.

(21) Appl. No.: 13/916,865

(22) Filed: Jun. 13, 2013

(65) Prior Publication Data
US 2014/0058314 A1  Feb. 27, 2014

Related U.S. Application Data

(63) Continuation of application No. 12/935,909, filed as application No. PCT/US2009/038942 on Mar. 31, 2009, now abandoned, and a continuation-in-part of application No. 12/440,815, filed as application No. PCT/AU2007/000728 on May 25, 2007.

(60) Provisional application No. 61/041,185, filed on Mar. 31, 2008.

(30) Foreign Application Priority Data

May 25, 2006 (AU) ................................ 2006902833

(51) Int. Cl.
| | | |
|---|---|---|
| A61N 1/18 | (2006.01) | |
| A61N 1/36 | (2006.01) | |
| A61N 1/05 | (2006.01) | |
| A61F 11/00 | (2006.01) | |

(52) U.S. Cl.
CPC .......... *A61N 1/36032* (2013.01); *A61N 1/0541* (2013.01); *A61F 11/00* (2013.01)
USPC ........................................................... 607/3

(58) Field of Classification Search
None
See application file for complete search history.

(56) References Cited

U.S. PATENT DOCUMENTS

| 4,922,926 A | 5/1990 | Hirschberg et al. |
|---|---|---|
| 6,263,225 B1 | 7/2001 | Howard, III |

(Continued)

FOREIGN PATENT DOCUMENTS

| WO | 02/41666 | 5/2002 |
|---|---|---|
| WO | 2006/083675 | 8/2006 |

OTHER PUBLICATIONS

International Search Report for International Application No. PCT/AU2007/000728 mailed Jul. 20, 2007 (4 pages).

(Continued)

*Primary Examiner* — Brian T Gedeon
*Assistant Examiner* — Ankit Tejani
(74) *Attorney, Agent, or Firm* — K&L Gates LLP

(57) ABSTRACT

A stimulating medical device comprising a stimulating assembly implantable proximate to nerve cells of a recipient having at least one agent delivery port and a plurality of electrical contacts; an electrical stimulation controller configured to generate electrical stimulation signals for application to a first population of the nerve cells via one or more of the plurality of electrical contacts; a pharmaceutical agent source configured to provide a pharmaceutical agent to the at least one delivery port for application to a second population of the nerve cells; and a pharmaceutical agent controller configured to control one or more of the pharmaceutical agent source and the at least one delivery port to cause selective application of the pharmaceutical agent to the second population of nerve cells.

11 Claims, 14 Drawing Sheets

(56) References Cited

U.S. PATENT DOCUMENTS

| | | |
|---|---|---|
| 6,309,410 B1 | 10/2001 | Kuzma et al. |
| 2004/0078057 A1 | 4/2004 | Gibson |
| 2004/0106953 A1 | 6/2004 | Yomtov et al. |
| 2004/0127942 A1 | 7/2004 | Yomtov et al. |
| 2005/0171579 A1 | 8/2005 | Tasche et al. |
| 2006/0287689 A1 | 12/2006 | Debruyne et al. |
| 2010/0256697 A1 | 10/2010 | Carter et al. |

OTHER PUBLICATIONS

International Search Report and Written Opinion for International Application No. PCT/US2009/038942 mailed May 28, 2009 (14 pages).

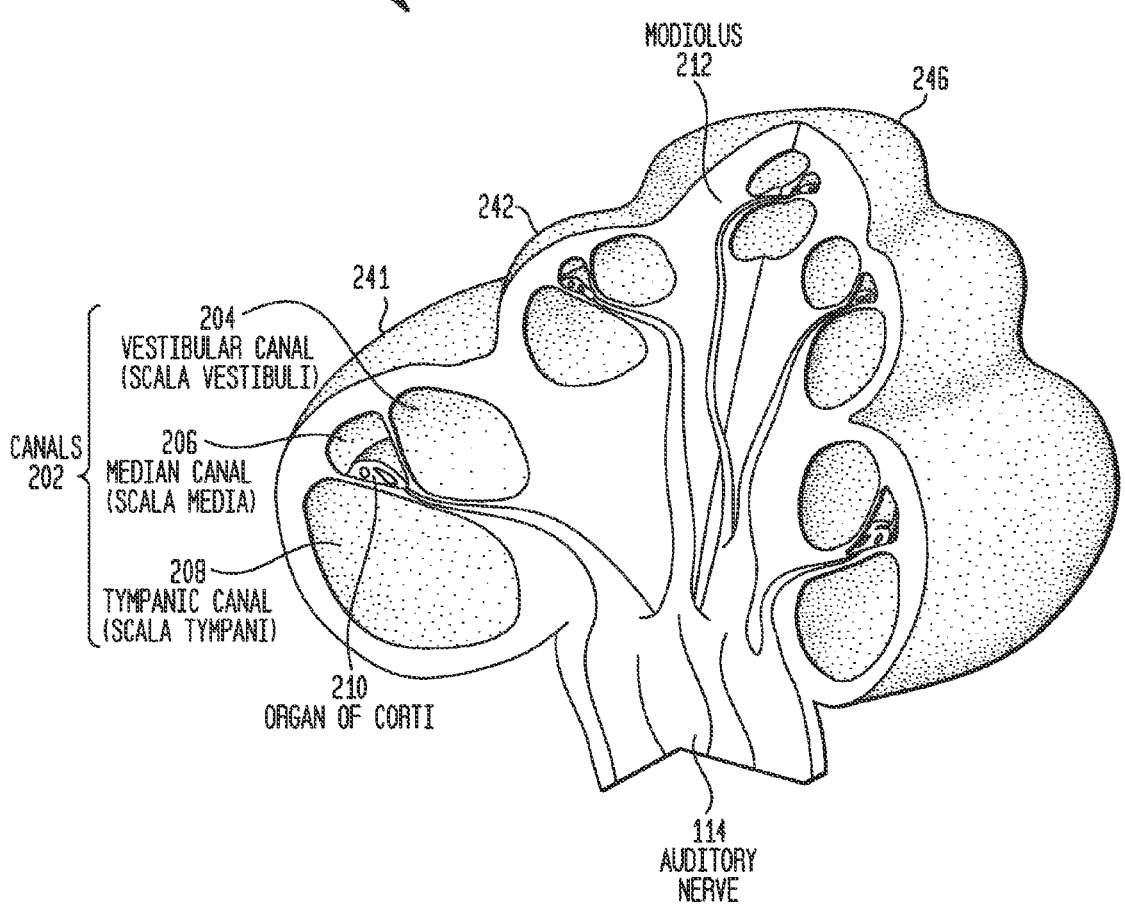

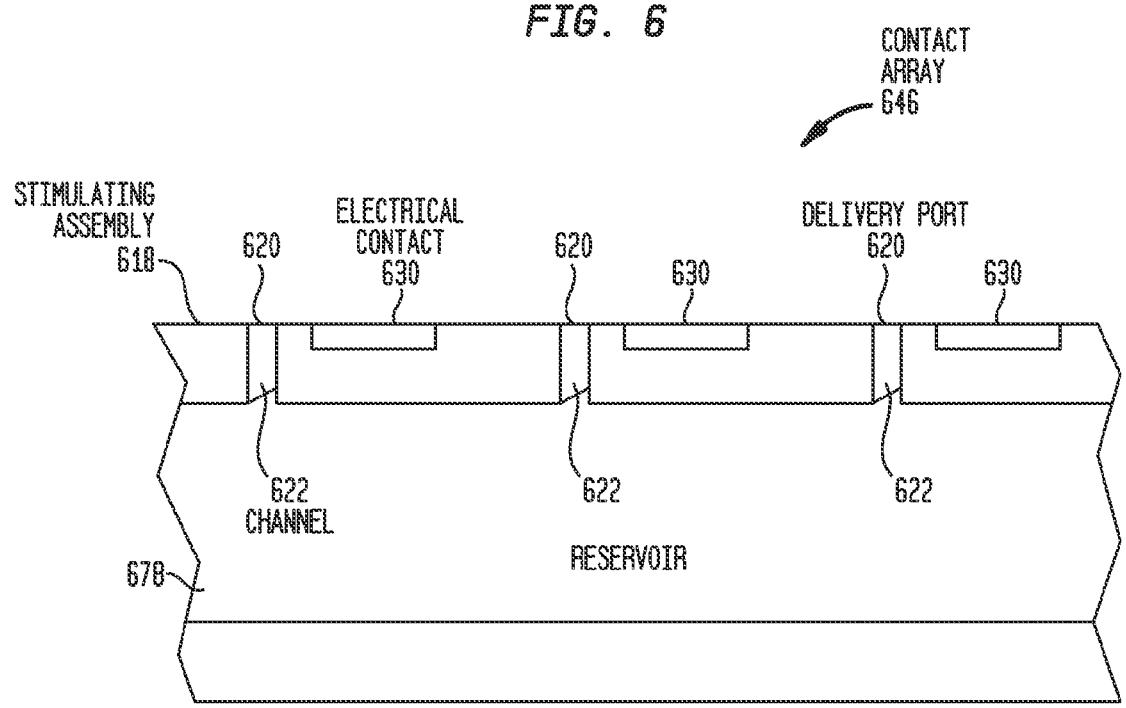

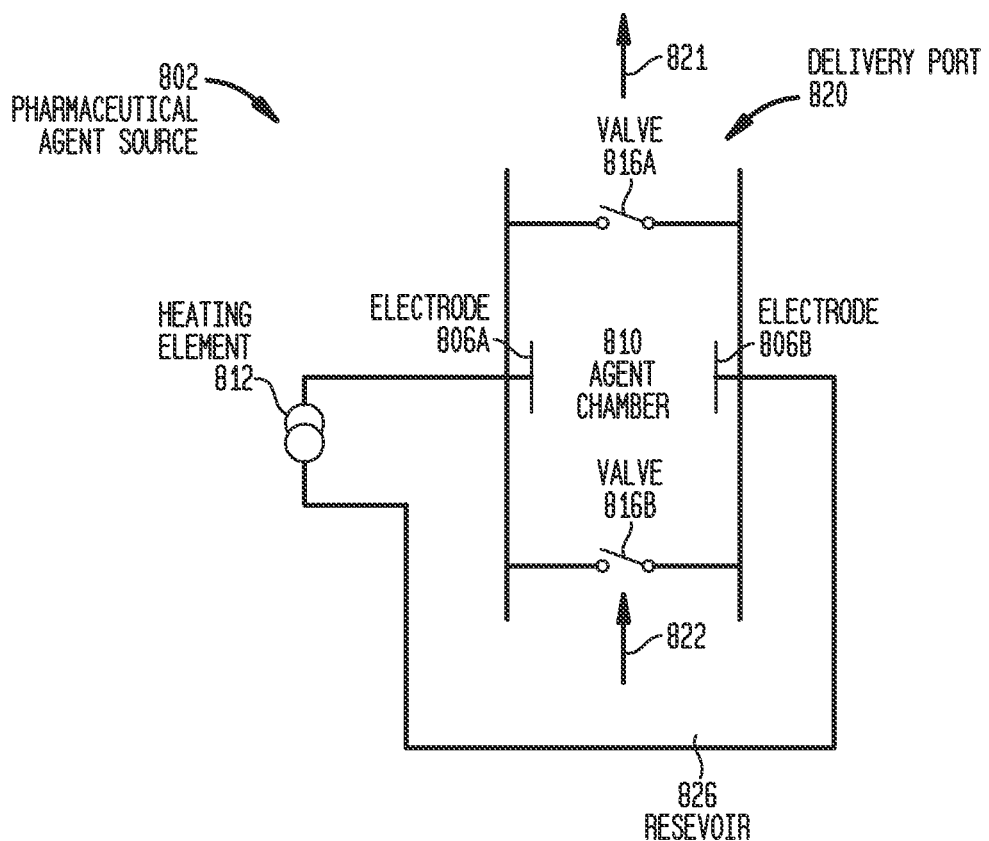
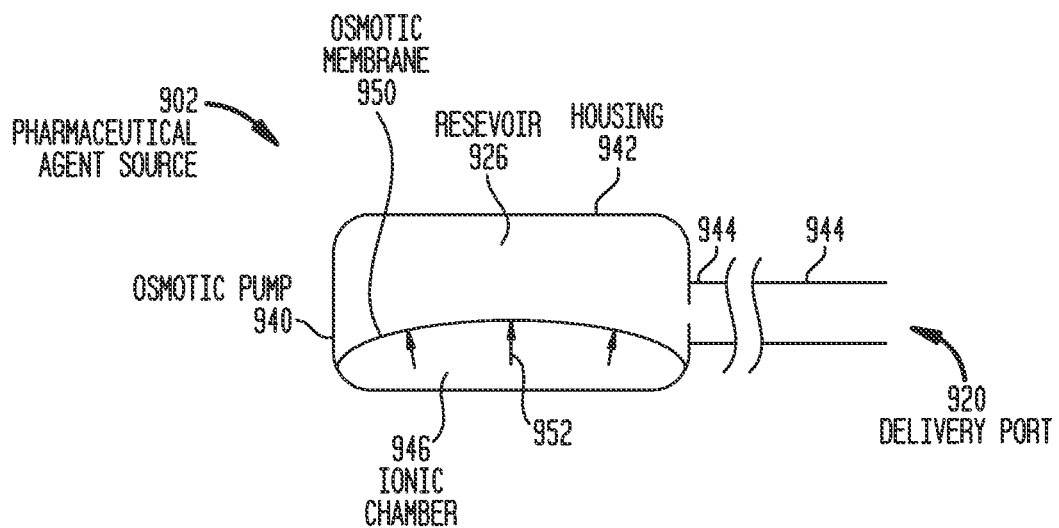

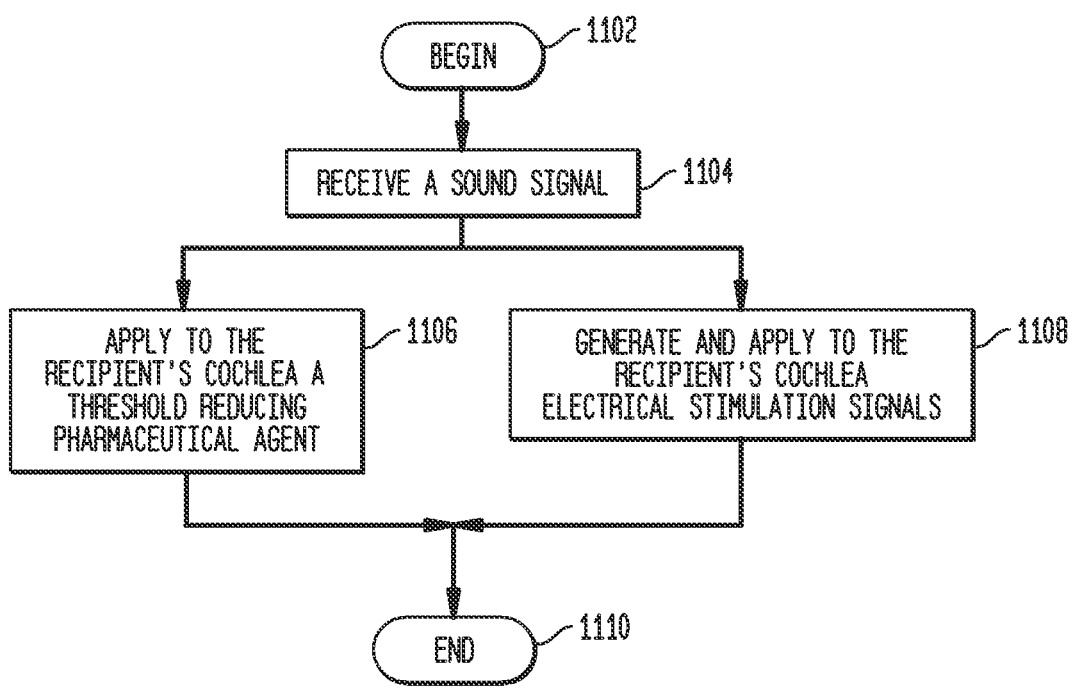

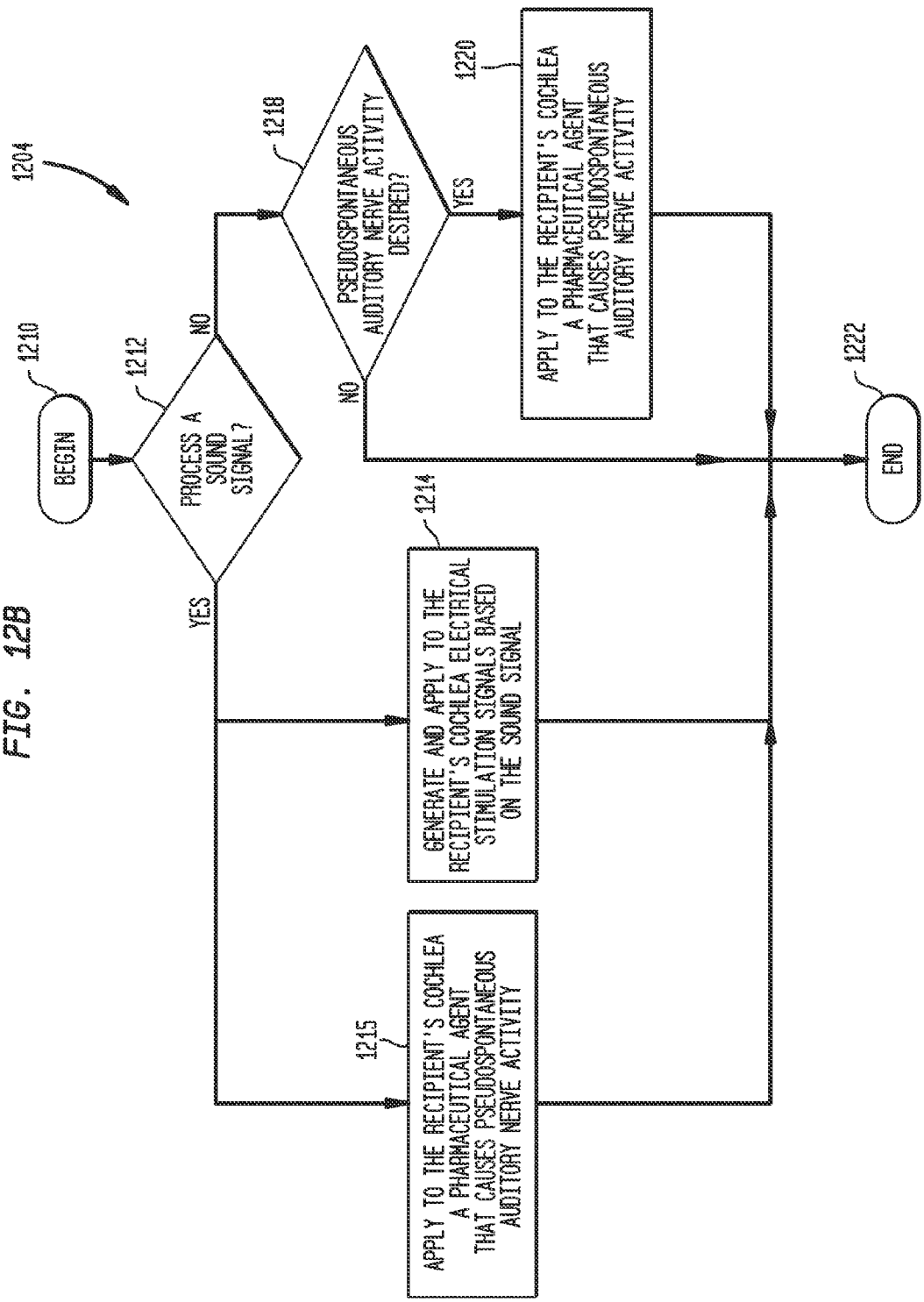

PHARMACEUTICAL AGENT DELIVERY IN A STIMULATING MEDICAL DEVICE

CROSS-REFERENCE TO RELATED APPLICATIONS

The present application is a Continuation application of U.S. patent application Ser. No. 12/935,909, filed Sep. 30, 2010, which is a National Stage application of International Application No. PCT/US2009/38942, filed Mar. 31, 2009, and claims the benefit of U.S. Provisional Patent Application 61/041,185; filed Mar. 31, 2008, which is hereby incorporated by reference herein. U.S. application Ser. No. 12/935,909 is a continuation-in-part of U.S. patent application Ser. No. 12/440,815, entitled "A Stimulating Medical Device," filed Mar. 11, 2009, which is a national stage application of PCT/AU07/00728, filed May 25, 2007, which claims priority to Australian Provisional Application No. AU 2006902833, filed May 25, 2006, the entire contents and disclosures of which are hereby incorporated by reference herein.

BACKGROUND

1. Field of the Invention

The present invention relates generally to a stimulating medical device and, more particularly, to pharmaceutical agent delivery in a stimulating medical device.

2. Related Art

Medical devices having one or more implantable components, generally referred to as implantable medical devices herein, have provided a wide range of therapeutic benefits to patients over recent decades. As such, the type of implantable devices and the range of functions performed thereby have increased over the years. Particular types of implantable medical devices, referred to as stimulating medical devices, are used to stimulate the nerve cells of the device recipient. A notable use for such stimulating medical devices is in recipients who suffer from various forms of hearing loss.

Hearing loss, which may be due to many different causes, is generally of two types, conductive and sensorineural. In some cases, a person suffers from hearing loss of both types. Conductive hearing loss occurs when the normal mechanical pathways for sound to reach the cochlea, and thus the sensory hair cells therein, are impeded, for example, by damage to the ossicles. Individuals who suffer from conductive hearing loss typically have some form of residual hearing because the hair cells in the cochlea are undamaged. As a result, individuals suffering from conductive hearing loss typically receive an acoustic hearing aid. Acoustic hearing aids stimulate an individual's cochlea by providing an amplified sound to the cochlea that causes mechanical motion of the cochlear fluid.

In many people who are profoundly deaf, however, the reason for their deafness is sensorineural hearing loss. Sensorineural hearing loss occurs when there is damage to the inner ear, or to the nerve pathways from the inner ear to the brain. As such, those suffering from some forms of sensorineural hearing loss are thus unable to derive suitable benefit from conventional acoustic hearing aids. As a result, hearing prostheses that apply electrical stimulation signals to nerve cells of the recipient's auditory system have been developed to provide the sensations of hearing to persons whom do not derive adequate benefit from conventional hearing aids. Such electrically-stimulating hearing prostheses apply electrical stimulation to nerve cells of the recipient's auditory system thereby providing the recipient with a hearing percept.

As used herein, the recipient's auditory system includes all sensory system components used to perceive a sound signal, such as hearing sensation receptors, neural pathways, including the auditory nerve and spiral ganglion, and parts of the brain used to sense sounds. Hearing prostheses that apply electrical stimulation signals to the recipient include, for example, auditory brain stimulators and cochlear prostheses (commonly referred to as cochlear prosthetic devices, cochlear implants, cochlear devices, and the like; simply "cochlear implants" herein.)

Oftentimes sensorineural hearing loss is due to the absence or destruction of the cochlear hair cells which transduce acoustic signals into nerve impulses. It is for this purpose that cochlear implants have been developed. Conventional cochlear implants provide a recipient with a hearing percept by delivering electrical stimulation signals directly to the auditory nerve cells, thereby bypassing absent or defective hair cells that normally transduce acoustic vibrations into neural activity. Such devices generally use an electrode array implanted in the cochlea so that the electrodes may differentially activate auditory neurons that normally encode differential pitches of sound.

SUMMARY

In one aspect of the present invention, a cochlear implant is provided. The cochlear implant comprises a stimulating assembly implantable in a cochlea of a recipient having at least one agent delivery port and a plurality of electrical contacts; an electrical stimulation controller configured to generate electrical stimulation signals for application to a first population of cochlea nerve cells via one or more of the plurality of electrical contacts; a pharmaceutical agent source configured to provide a pharmaceutical agent to the at least one delivery port for application to a second population of cochlea nerve cells; and a pharmaceutical agent controller configured to control one or more of the pharmaceutical agent source and the at least one delivery port to cause selective application of the pharmaceutical agent to the second population of nerve cells.

In another aspect of the present invention, a method for stimulating the cochlear of a recipient with a cochlear implant comprising a stimulating assembly implantable in a cochlea of a recipient having at least one agent delivery port and a plurality of electrical contacts is provided. The method comprises: generating electrical stimulation signals; applying the electrical stimulation signals to a first population of cochlea nerve cells via one or more of the plurality of electrical contacts; applying a pharmaceutical agent to a second population of cochlea nerve cells via the at least one delivery port.

In a still other aspect of the present invention, a stimulating medical device is provided. The stimulating medical device comprises a stimulating assembly implantable proximate to nerve cells of a recipient having at least one agent delivery port and a plurality of electrical contacts; an electrical stimulation controller configured to generate electrical stimulation signals for application to a first population of the nerve cells via one or more of the plurality of electrical contacts; a pharmaceutical agent source configured to provide a pharmaceutical agent to the at least one delivery port for application to a second population of the nerve cells; and a pharmaceutical agent controller configured to control one or more of the pharmaceutical agent source and the at least one delivery port to cause selective application of the pharmaceutical agent to the second population of nerve cells.

BRIEF DESCRIPTION OF THE DRAWINGS

Embodiments of the present invention are described below with reference to the attached drawings, in which:

FIG. 2A is a perspective, partially cut-away view of a cochlea exposing the canals and nerve fibers of the cochlea;

FIG. 6 is a cross-sectional side view of a portion of a stimulating assembly in accordance with embodiments of the present invention;

FIG. 8 is a diagram of a pharmaceutical agent source in accordance with embodiments of the present invention;

FIG. 9 is a diagram of a pharmaceutical agent source in accordance with embodiments of the present invention;

FIG. 11 is a flowchart illustrating the operations performed by a cochlear implant in accordance with embodiments of the present invention;

FIG. 12B is a detailed flowchart illustrating the operations performed by a cochlear implant in accordance with embodiments of FIG. 12A.

DETAILED DESCRIPTION

Aspects of the present invention are generally directed to a stimulating medical device configured to apply a pharmaceutical agent to the nerve cells of a recipient. The stimulating medical device delivers the pharmaceutical agent alone, or in combination with electrical stimulation signals.

In particular embodiments, the stimulating medical device comprises an implantable stimulating assembly having delivery ports and electrical contacts. A pharmaceutical agent source delivers pharmaceutical agents to the recipient's nerve cells via the delivery ports, and an electrical stimulation controller generates electrical stimulation signals that are applied to the nerve cells via the electrical contacts.

Embodiments of the present invention may be implemented in various types of stimulating medical devices such as functional electrical stimulators, cochlear prostheses, auditory brain stimulators, etc. As noted, cochlear implants stimulate auditory nerve cells, bypassing absent or defective hair cells that normally transduce acoustic vibrations into neural activity. Conventional cochlear implants generally use an array of electrodes, sometimes referred to as electrical contacts herein, inserted into or adjacent the cochlea so that the electrical contacts may activate auditory neurons that normally encode differential pitches of sound. Auditory brain stimulators are used to treat a smaller number of recipients, such as those with bilateral degeneration of the auditory nerve. The auditory brain stimulator comprises an array of electrical contacts configured to be positioned, for example, proximal to the recipient's brainstem. When implanted, the electrical contacts apply electrical stimulation signals to the cochlear nucleus in the brainstem, resulting in a hearing sensation by the recipient. For ease of illustration, the present invention will be described herein primarily in connection with cochlear implants. However, it should be appreciated that embodiments of the present invention, regardless of whether described herein, may be implemented in any stimulating medical device now known or later developed.

Figure 1:
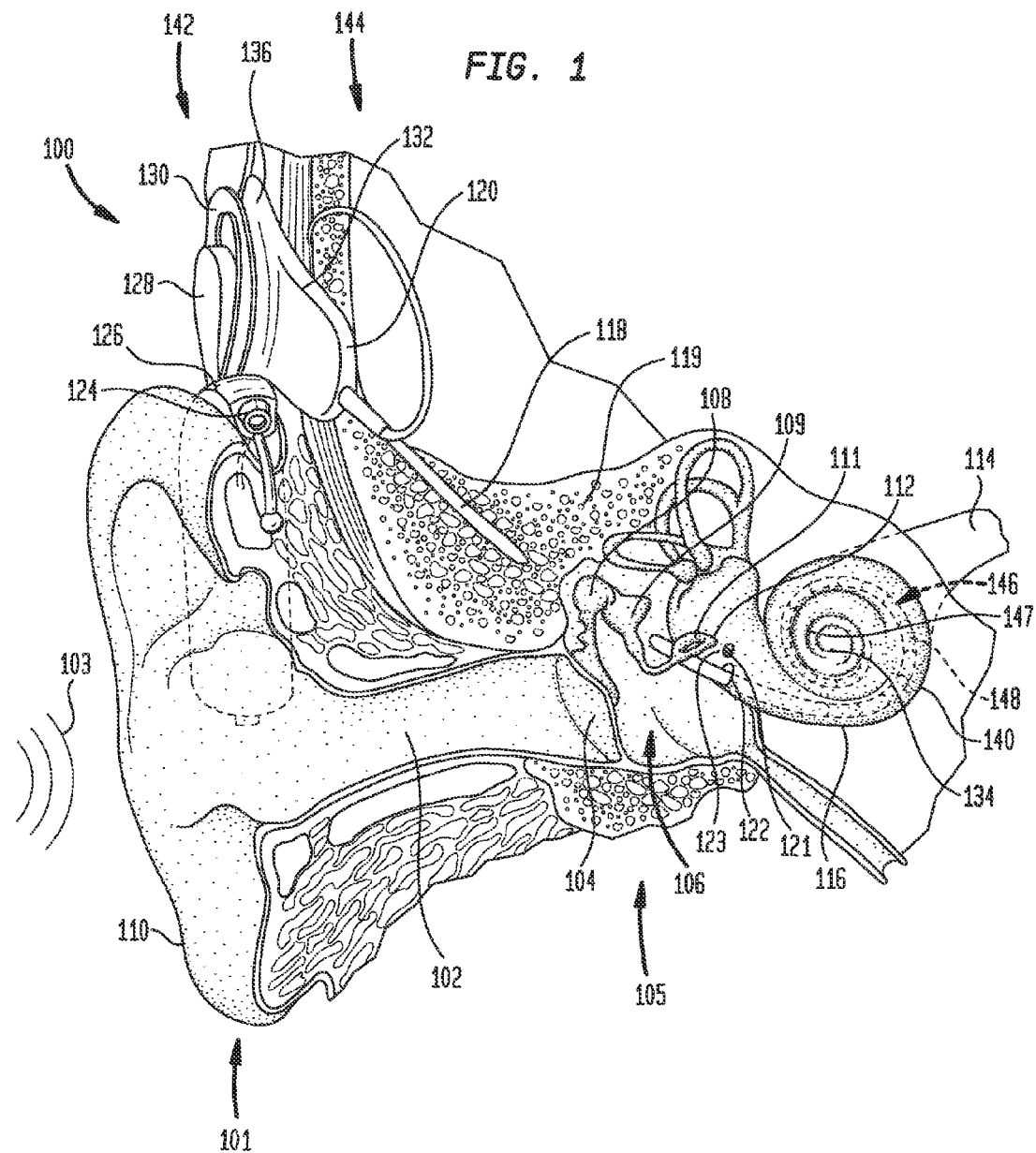
FIG. 1 is a perspective view of an implanted cochlear implant which may be advantageously configured to implement embodiments of the present invention.

FIG. 1 is a perspective view of an exemplary cochlear implant 100 in which embodiments of the present invention may be implemented. The relevant components of the recipient's ear are described below, followed by a description of cochlear implant 100.

In a fully functional ear, outer ear 101 comprises an auricle 110 and an ear canal 102. An acoustic pressure or sound wave 103 is collected by auricle 110 and channeled into and through ear canal 102. Disposed across the distal end of ear cannel 102 is a tympanic membrane 104 which vibrates in response to sound wave 103. This vibration is coupled to oval window or fenestra ovalis 112 through three bones of middle ear 105, collectively referred to as the ossicles 106 and comprising the malleus 108, the incus 109 and the stapes 111. Bones 108, 109 and 111 of middle ear 105 serve to filter and amplify sound wave 103, causing oval window 112 to articulate, or vibrate in response to vibration of tympanic membrane 104. This vibration sets up waves of fluid motion of the perilymph within cochlea 140. Such fluid motion, in turn, activates tiny hair cells (not shown) inside cochlea 140. Activation of the hair cells causes appropriate nerve impulses to be generated and transferred via neural pathways through the spiral ganglion cells (not shown) and auditory nerve 114 to the brain (also not shown) where they are perceived as sound.

Cochlear implant 100 comprises an external component 142 which is directly or indirectly attached to the body of the recipient, and an internal component 144 which is temporarily or permanently implanted in the recipient. External component 142 typically comprises one or more acoustic pickup devices, such as microphone 124, for detecting sound, a sound processing unit 126, a power source (not shown), and an external transmitter unit 128. External transmitter unit 128 comprises an external coil 130 and, preferably, a magnet (not shown) secured directly or indirectly to external coil 130. Sound processing unit 126 processes the output of a sound input component, shown as microphone 124 that is positioned in the depicted embodiment adjacent to auricle 110 of the recipient. Sound processing unit 126 generates encoded signals, sometimes referred to herein as encoded data signals, which are provided to external transmitter unit 128 via a cable (not shown).

Internal component 144 comprises, in this depicted embodiment, an internal receiver unit 132, a stimulator unit 120, and an elongate stimulating assembly 118. Internal receiver unit 132 comprises an internal coil 136, and preferably, a magnet (also not shown) fixed relative to the internal coil. Internal receiver unit 132 and stimulator unit 120 are hermetically sealed within a biocompatible housing, sometimes collectively referred to as a stimulator/receiver unit. The magnets facilitate the operational alignment of the external and internal coils, enabling internal coil 136 to receive power and stimulation data from external coil 130, as noted above. Elongate stimulating assembly 118 has a proximal end connected to stimulator unit 120, and a distal end implanted in cochlea 140. Electrode assembly 118 extends from stimulator unit 120 to cochlea 140 through mastoid bone 119. In some embodiments, stimulating assembly 118 may be implanted at least in basal region 116, and sometimes further. For example, stimulating assembly 118 may extend towards apical end of cochlea 140, referred to as cochlea apex 134. In certain circumstances, stimulating assembly 118 may be inserted into cochlea 140 via a cochleostomy 122. In other circumstances, a cochleostomy may be formed through round window 121, oval window 112, the promontory 123 or through an apical turn 147 of cochlea 140.

Stimulating assembly 118 comprises a longitudinally aligned and distally extending array 146 of stimulating electrical contacts 148, sometimes referred to as contact array 146 herein, disposed along a length thereof. Although contact array 146 may be disposed on stimulating assembly 118, in most practical applications, contact array 146 is integrated into stimulating assembly 118. As such, for all embodiments of stimulating assembly 118, contact array 146 is generally referred to herein as being disposed in stimulating assembly 118. As described below, stimulator unit 120 generates stimulation signals which are applied by contacts 148 to cochlea 140, thereby stimulating auditory nerve 114. Also as described below, stimulating assembly 118 comprises one or more delivery ports (not shown) to deliver a pharmaceutical agent to cochlea nerve cells.

In certain embodiments, external coil 130 transmits electrical signals (i.e., power and stimulation data) to internal coil 136 via a radio frequency (RF) link, as noted above. Internal coil 136 is typically a wire antenna coil comprised of multiple turns of electrically insulated single-strand or multi-strand platinum or gold wire. The electrical insulation of internal coil 136 is provided by a flexible silicone molding (not shown). In use, implantable receiver unit 132 may be positioned in a recess of the temporal bone adjacent auricle 110 of the recipient.

Although FIG. 1 illustrates a cochlear implant 100 having an external component 142, it should be appreciated that embodiments of the present invention may be implemented in other cochlear implant embodiments, such as a totally implantable cochlear implant.

Figure 2B:
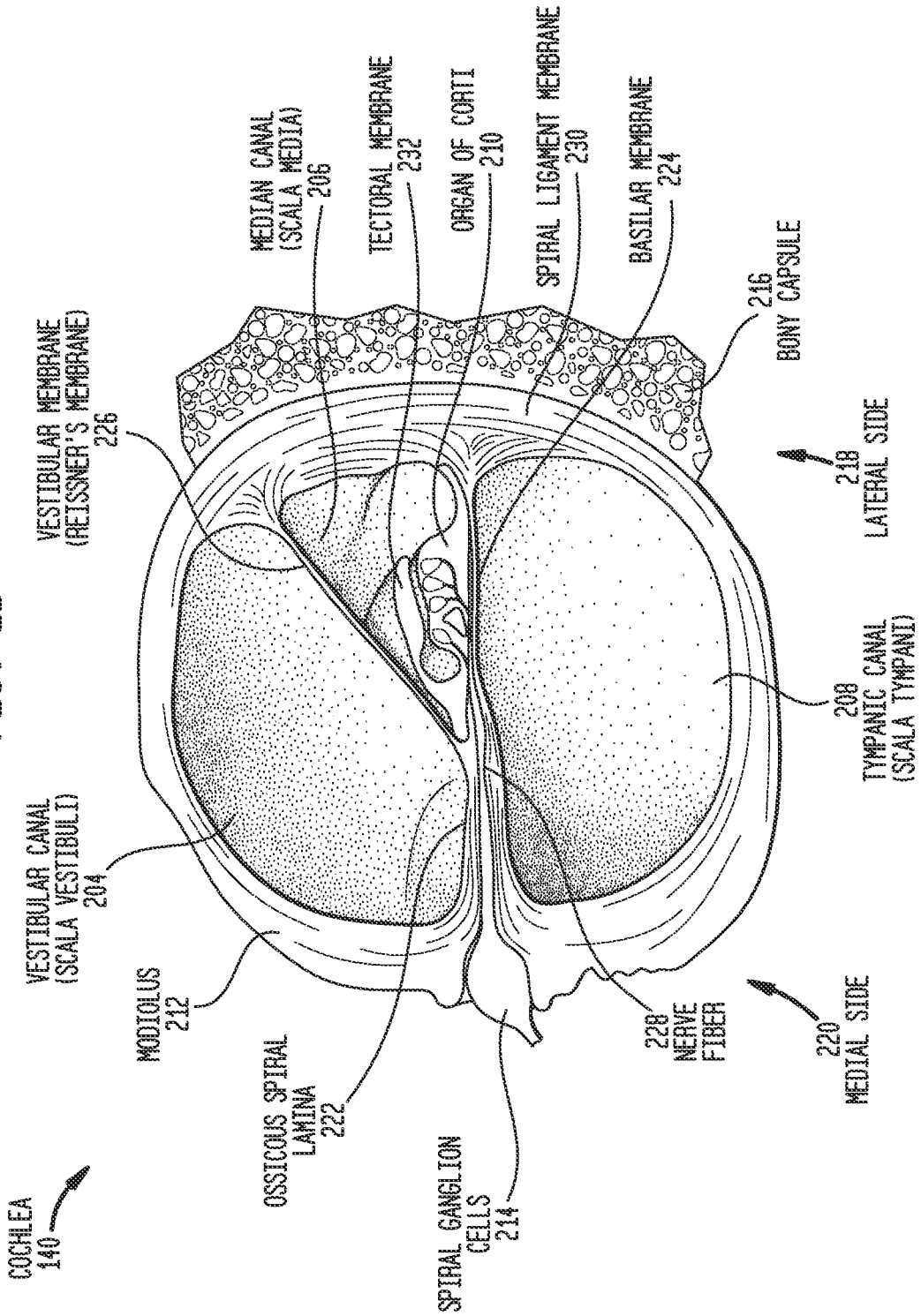
FIG. 2B is a cross-sectional view of one turn of the canals of a human cochlea.

Relevant aspects of cochlea 140 are described next below with reference to FIGS. 2A and 2B is a perspective view of cochlea 140 partially cut-away to display the canals and nerve fibers of the cochlea. FIG. 2B is a cross-sectional view of one turn of the canals of cochlea 140. To facilitate understanding, the following description will reference the cochlea illustrated in FIGS. 2A and 2B as cochlea 140, which was introduced above with reference to FIG. 1.

Referring to FIG. 2A, cochlea 140 is a conical spiral structure comprising three parallel fluid-filled canals or ducts, collectively and generally referred to herein as canals 202. Canals 202 comprise the tympanic canal 208, also referred to as the scala tympani 208, the vestibular canal 204, also referred to as the scala vestibuli 204, and the median canal 206, also referred to as the scala media 206. Cochlea 140 has a conical shaped central axis, the modiolus 212, that forms the inner wall of scala vestibuli 204 and scala tympani 208. Tympanic and vestibular canals 208, 204 transmit pressure, while medial canal 206 contains the organ of corti 210 which detects pressure impulses and responds with electrical impulses which travel along auditory nerve 114 to the brain (not shown).

Cochlea 140 spirals about modiolus 212 several times and terminates at cochlea apex 134. Modiolus 212 is largest near its base where it corresponds to first turn 241 of cochlea 140. The size of modiolus 212 decreases in the regions corresponding to medial 242 and apical turns 246 of cochlea 140.

Referring now to FIG. 2B, separating canals 202 of cochlear 140 are various membranes and other tissue. The Ossicous spiral lamina 222 projects from modiolus 212 to separate scala vestibuli 204 from scala tympani 208. Toward lateral side 218 of scala tympani 208, a basilar membrane 224 separates scala tympani 208 from scala media 206. Similarly, toward lateral side 218 of scala vestibuli 204, a vestibular membrane 226, also referred to as the Reissner's membrane 226, separates scala vestibuli 204 from scala media 206.

Portions of cochlea 140 are encased in a bony capsule 216. Bony capsule 216 resides on lateral side 218 (the right side as illustrated in FIG. 2B), of cochlea 140. Spiral ganglion cells 214 reside on the opposing medial side 220 (the left side as illustrated in FIG. 2B) of cochlea 140. A spiral ligament membrane 230 is located between lateral side 218 of spiral tympani 208 and bony capsule 216, and between lateral side 218 of scala media 206 and bony capsule 216. Spiral ligament 230 also typically extends around at least a portion of lateral side 218 of scala vestibuli 204.

The fluid in tympanic and vestibular canals 208, 204, referred to as perilymph, has different properties than that of the fluid which fills scala media 206 and which surrounds organ of Corti 210, referred to as endolymph. Sound entering auricle 110 causes pressure changes in cochlea 140 to travel through the fluid-filled tympanic and vestibular canals 208, 204. As noted, organ of Corti 210 is situated on basilar membrane 224 in scala media 206. It contains rows of 16,000-20,000 hair cells (not shown) which protrude from its surface. Above them is the tectoral membrane 232 which moves in response to pressure variations in the fluid-filled tympanic and vestibular canals 208, 204. Small relative movements of the layers of membrane 232 are sufficient to cause the hair cells in the endolymph to move thereby causing the creation of a voltage pulse or action potential which travels along the associated nerve fiber 228. Nerve fibers 228, embedded within spiral lamina 222, connect the hair cells with the spiral ganglion cells 214 which form auditory nerve 114. The action potential is relayed via neural pathways through the auditory nerve 114 to the auditory areas of the brain (not shown) for processing.

The place along basilar membrane 224 where maximum excitation of the hair cells occurs determines the perception of pitch and loudness according to the place theory. Due to this anatomical arrangement, cochlea 140 has characteristically been referred to as being "tonotopically mapped." That is, regions of cochlea 140 toward basal region 116 are responsive to high frequency signals, while regions of cochlea 140 toward apical end 147 are responsive to low frequency signals. These tonotopical properties of cochlea 140 are exploited in a cochlear implant by delivering stimulation signals within a predetermined frequency range to a region of the cochlea that is most sensitive to that particular frequency range.

As is well known in the art, the human auditory system is composed of many structural components, some of which are connected extensively by neural pathways comprising bundles of nerve cells (neurons). Each nerve cell has a cell membrane which acts as a barrier to prevent intercellular fluid from mixing with extracellular fluid. The intercellular and extracellular fluids have different concentrations of ions, which leads to a difference in charge between the fluids. This difference in charge across the cell membrane is referred to herein as the membrane potential (Vm) of the nerve cell. Nerve cells use membrane potentials to transmit signals between different parts of the auditory system.

In nerve cells that are at rest (i.e., not transmitting a nerve signal) the membrane potential is referred to as the resting potential of the nerve cell. Upon receipt of a stimulus, the electrical properties of a nerve cell membrane are subjected to abrupt changes, referred to herein as a nerve action potential, or simply action potential. The action potential represents the transient depolarization and repolarization of the nerve cell membrane. The action potential causes electrical signal transmission along the conductive core (axon) of a nerve cell. Signals may be then transmitted along a group or population of nerve cells via such propagating action potentials.

Figure 3:
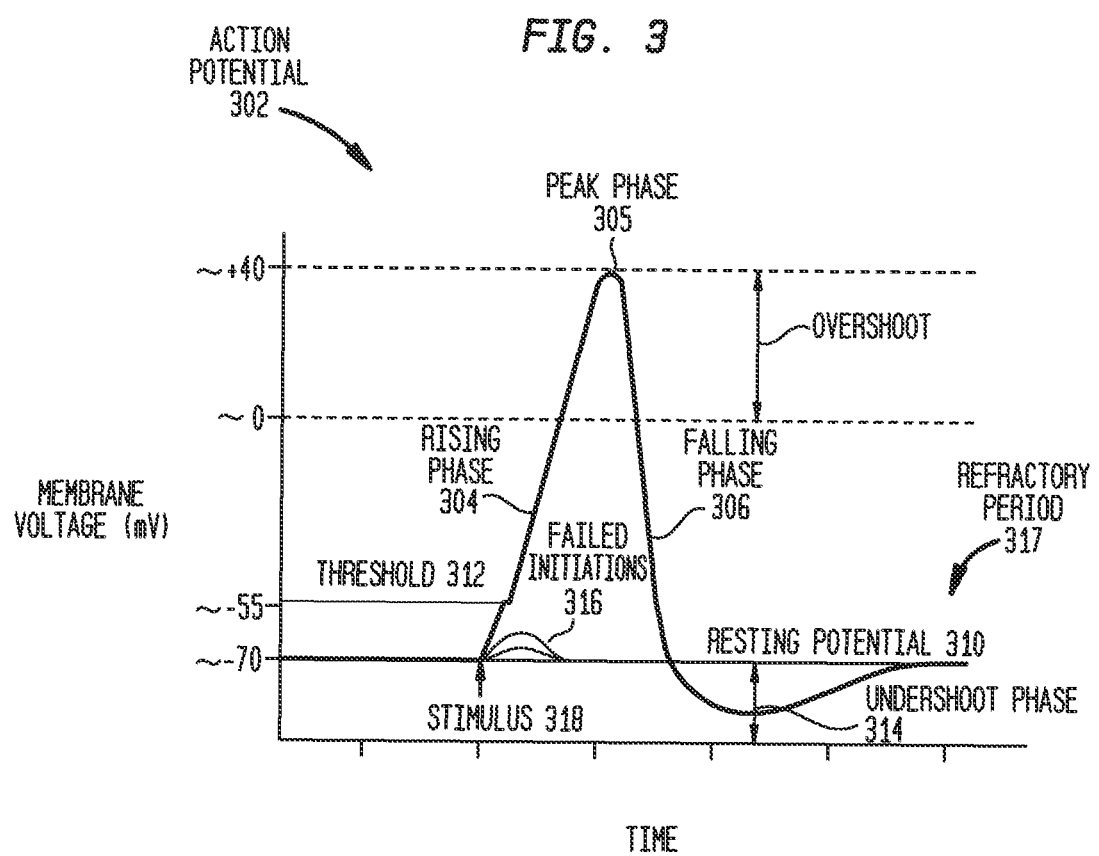
FIG. 3 is graph illustrating the various phases of an idealized action potential as the potential passes through a nerve cell, illustrated in membrane voltage versus time.

FIG. 3 is graph illustrating the various phases of an idealized action potential 302 as the potential passes through a nerve cell in accordance with embodiments of the present invention. The action potential is presented as membrane voltage in millivolts (mV) versus time. As would be appreciated by one of ordinary skill in the art, the membrane voltages and times shown in FIG. 3 are provided for illustration purposes only. The actual voltages may vary depending on the individual. As such, this illustrative example should not be construed as limiting the present invention.

In the example of FIG. 3, prior to application of a stimulus 318 to the nerve cell, the resting potential 310 of the nerve cell is approximately −70 mV. Stimulus 318 is applied at a first time. In normal hearing, this stimulus is provided as a result of the movement of the hair cells of the cochlea. Movement of these hair cells results in the release of a nerve impulse. As discussed in greater detail below, in embodiments of the present invention the stimulus results from the application of one or more of an electrical stimulation signal and a therapeutic agent to the nerve cell.

As shown in FIG. 3, following application of stimulus 318, the nerve cell begins to depolarize. Depolarization of the nerve cell refers to the fact that the voltage of the cell becomes more positive following stimulus 318. When the membrane of the nerve cell becomes depolarized beyond the cell's critical threshold, the nerve cell undergoes an action potential. This action potential is sometimes referred to as the "firing" of the nerve cell. As used herein, the critical threshold of a nerve cell, group of nerve cells, etc. refers to the threshold level at which the nerve cell, group of nerve cells, etc. will undergo an action potential. In the example illustrated in FIG. 3, the critical threshold level 312 for firing of the nerve cell is approximately −50 mV. As would be appreciated, the critical threshold and other transitions may be different for various recipients. As such, the values provided in FIG. 3 are merely illustrative. For consistency, a critical threshold of −50 mV will be used herein, but such usage should not be considered to limit the present invention The course of this action potential in the nerve cell can be generally divided into five phases. These five phases are shown in FIG. 3 as a rising phase 304, a peak phase 305, a falling phase 306, an undershoot phase 314, and finally a refractory period 317. During rising phase 304, the membrane voltage continues to depolarize. The point at which depolarization ceases is shown as peak phase 305. In the illustrative embodiment of FIG. 3, at this peak phase 305, the membrane voltage reaches a maximum value of approximately 40 mV.

Following peak phase 305, the action potential underfoes falling phase 306. During falling phase 306, the membrane voltage becomes increasingly more negative, sometimes referred to as hyperpolarization of the nerve cell. This hyperpolarization causes the membrane voltage to temporarily become more negatively charged then when the nerve cell is at rest. This phase is referred to as the undershoot phase 314 of action potential 302. Following this undershoot, there is a time period during which it is impossible or difficult for the nerve cells to fire. This time period is referred to as refractory period 317.

Action potential 302 illustrated in FIG. 3 may travel along, for example the auditory nerve, without diminishing or fading out because the action potential is regenerated each nerve cell. This regeneration occurs because an action potential at one nerve cell raises the voltage at adjacent nerve cells. This induced rise in voltage depolarizes adjacent nerve cells thereby provoking a new action potential therein.

As noted above, the nerve cell must obtain a membrane voltage above a critical threshold before the nerve cell may fire. Illustrated in FIG. 3 are several failed initiations 316 which occur as a result of stimuli which were insufficient to raise the membrane voltage above the critical threshold value to result in an action potential.

In normal hearing there is a level of spontaneous or random nerve activity in the absence of sound that is inaudible to an individual. This spontaneous nerve activity is the result of the random release of neurotransmitters by the cochlea hair cells. When a neurotransmitter is randomly released (in the absence of sound), the neurotransmitter causes the spontaneous firing of an auditory nerve cell. Many of these combine to cause a level of inherent background noise. However, in cochlear implant recipients and other individuals, such as individuals suffering from tinnitus, this spontaneous nerve activity is lacking.

One aspect of the present invention is directed to invoking stochastic or random activity within a nerve cell, referred to as pseudospontaneous nerve activity, through the delivery of one or more pharmaceutical agents to the recipient's cochlea. In certain embodiments, this pseudospontaneous nerve activity replicates the spontaneous or random nerve activity experienced by individuals with normal hearing. By replicating the naturally occurring spontaneous activity cochlear implants may provide stimulated hearing that more closely replicates natural hearing. This may advantageously facilitate more accurate speech perceptions and/or the suppression of tinnitus.

In these embodiments of the present invention, the cochlear implant applies threshold reducing pharmaceutical agents such as a brain derived neurotrophic factor (BDNF), an ionic species such as sodium or potassium, etc., to a population of cochlea nerve cells. These applied pharmaceutical agents encourage, facilitate or allow the pseudospontaneous nerve activity that is below the recipient's perception or auditory threshold. Specifically, the pharmaceutical agent is used to lower the firing threshold of the nerve to the point where a particular background spontaneous nerve firing rate is achieved. The spontaneous firing of the nerve cells is unperceivable by the recipient. As used herein, pharmaceutical agents refer to any artificial or naturally occurring drug, medicine, pharmaceutical, hormone suitable for the desired purpose.

As noted above, electrical stimulation signals applied to a recipient's cochlea must have a minimum intensity in order to evoke a hearing percept. Specifically, the electrical stimulation signals must have an intensity which increases the membrane voltage of the cells from the resting level (resting potential) to a level at which the nerve cells will fire, referred to as the recipient's auditory threshold level. Certain embodiments of the present invention reduce the intensity required of electrical stimulations to evoke a hearing percept by delivering a threshold reducing pharmaceutical agent to the cochlea prior to or during application of electrical stimulation signals. Therefore, because the nerve cells will fire more readily, hearing percepts may be evoked using lower intensity electrical stimulation signals.

In an alternative embodiment of the present invention, the cochlear implant is configured to apply pharmaceutical agents to the recipient's cochlea to evoke a hearing percept. As discussed in greater detail below, these embodiments apply the pharmaceutical agents under the control of a speech processor so that the recipient may perceive a sound signal received by the cochlear implant.

In further aspects of the present invention, a pharmaceutical agent is delivered to a recipient's nerve cells to increase neural survival. For example, cochlear nerve cells which are not used to receive a hearing percept will eventually become non-functional. In other words, non-used spiral ganglion or other cells will die and thus lose the ability to transmit electrical potentials. Certain aspects of the present invention are directed to increasing the neural survival rate of such unused cochlear nerve cells in a cochlear implant recipient. In these aspects, a pharmaceutical agent is delivered to the non-used nerve cells to cause the nerve cells to fire, thereby prolonging the cell's usable life span. The firing of these nerve cells is unperceivable by the recipient.

Figure 4:
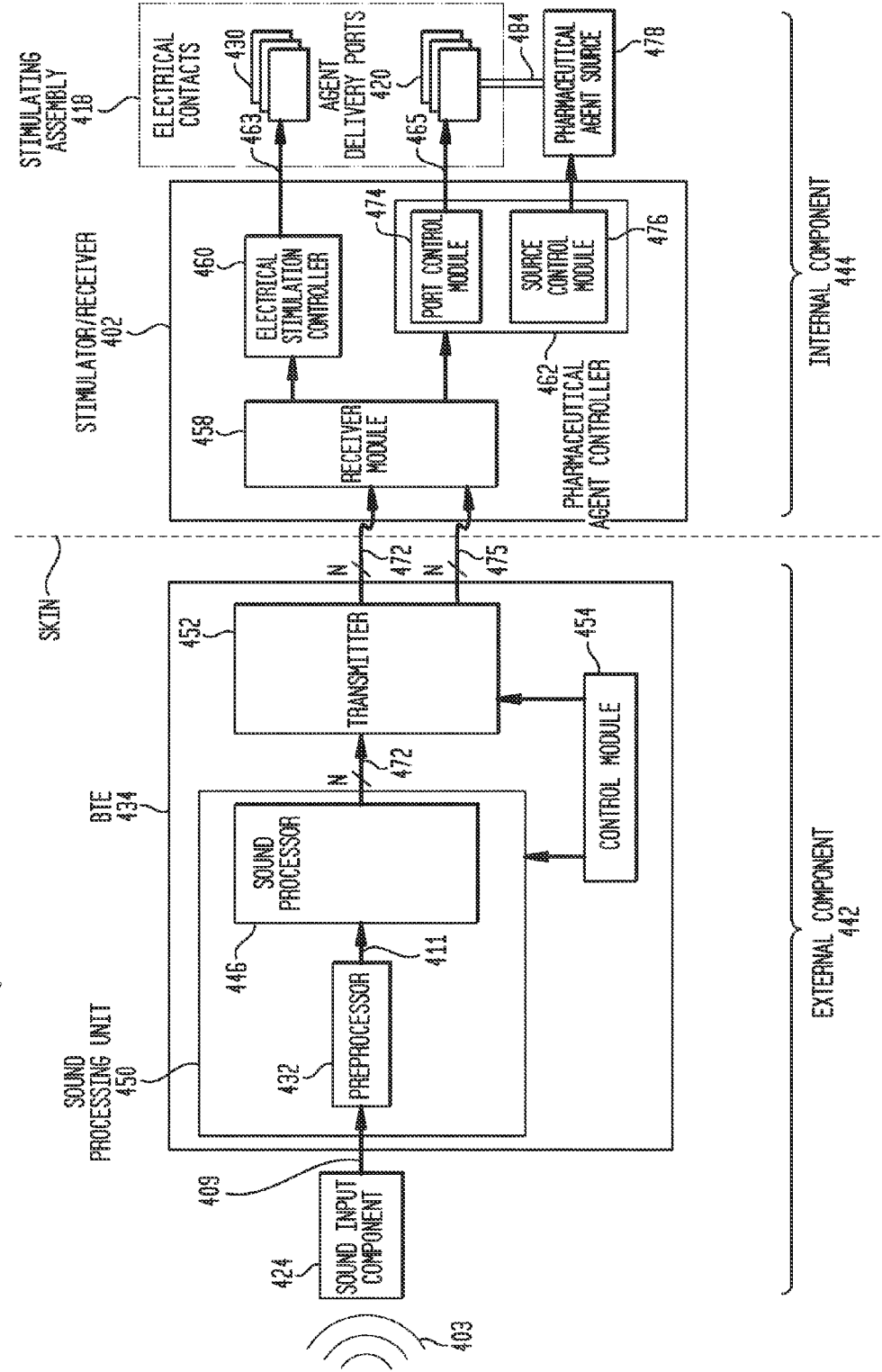
FIG. 4 is a detailed functional block diagram illustrating the components of a cochlear implant in accordance with embodiments of the present invention.

FIG. 4 is a detailed functional block diagram of a cochlear implant 400 that may be used to implement the above and other embodiments of the present invention. As shown, elements of cochlear implant 400 that have substantially the same or similar structures and/or perform substantially the same or similar functions as elements of cochlear implant 100 are illustrated in FIG. 4 using a 400 series reference number having two right digits which are the same as the right two digits as the corresponding element of FIG. 1. For example, as shown, cochlear implant 400 comprises an embodiment of external component 142 of FIG. 1, referred to as external component 442.

In the illustrative embodiment of FIG. 4, external component 442 comprises a behind-the-ear (BTE) device 434 and one or more sound input components 424. Sound input component 424 is configured to receive a sound signal 203. Sound input component 424 may comprise, for example, one or more microphones, a telecoil, or an electrical input which connects cochlear implant 400 to FM hearing systems, MP3 players, musical instruments, computers, televisions, mobile phones, etc. As such, sound signal 403 may comprise a sound wave or an electrical audio signal. In the embodiment of FIG. 4, sound input component 424 comprises a sound input component 424 which may be a directional microphone and/or an omni-directional microphone. Sound input component 424 outputs signals 409 representing received sound signal 403 to sound processing unit 450 within BTE 434.

BTE 434 is configured to be worn behind the ear of the recipient and, as described herein, may comprise various sound processing and other components. Sound input component 424 may be positionable on BTE 434 or elsewhere on the recipient.

As would be appreciated by those of ordinary skill in the art, although the embodiments of FIG. 4 are described with reference to external component 442 configured as a BTE, other configurations of external component 442 may also be implemented in embodiments of the present invention. For example, in certain embodiments, external component 442 may be configured as a body-worn sound processing unit instead of, or in combination with, a component that is worn behind the ear. In other embodiments, external component 442 may be omitted and sound input component 424 as well as the components residing in BTE device 434 may be implanted in the recipient. Such an arrangement of a cochlear implant is sometimes referred to as a totally-implantable cochlear implant. For ease of description, embodiments of the present invention will be primarily described herein with reference to cochlear implants having external components. However, embodiments of the present invention may be equally implemented in any cochlear implant now known or later developed.

BTE device 434 comprises a sound processing unit 450, a transmitter 452 and a control module 454. As noted above, sound input component 424 receives a sound signal and delivers corresponding electrical signals 409 to a preprocessor 432 of sound processing unit 450. Prep-processor 432 may comprise various combinations of preamplifiers, automatic gain controllers, and Analog-to Digital-Converters used to convert signal 409 in a digital signal 411 for use by sound processor 446.

As would be appreciated, in certain embodiments of the present invention, pre-processor 432 may be implemented as a component of sound input component 424. It should also be appreciated that in certain embodiments, one or more components of pre-processor module 432 may not be necessary. For example, in certain embodiments, sound signal 403 received by sound input component 424 comprises a digitized signal received from, for example, a FM hearing system, MP3 player, television, mobile phones, etc. In these embodiments, the received signal may be provided directly to sound processor 446.

Sound processor 446 performs sound processing operations to convert electrical signals 411 received from preprocessor 432 into one or more encoded data signals 472 which are then transmitted to internal component 444 by transmitter 452. There are numerous strategies that may be implemented by sound processor 446 to convert signals 411 into encoded data signals 472. Embodiments of the present invention may be used in combination with any processing strategy now or later developed.

Embodiments of cochlear implant 400 may locally store several processing strategies as a software program or otherwise, any one of which may be selected depending, for example, on the recipient's listening environment. For example, a recipient may choose one strategy for a low noise environment, such as a conversation in an enclosed room, and a second strategy for a high noise environment, such as on a public street. The programmed speech strategies may be different versions of the same speech strategy, each programmed with different parameters or settings.

External component 442 may further comprise a control module 454. Control module 454 may be configured to receive control inputs from a recipient, an external device, or internally generated events, commands or interrupts. Control module 454 controls sound processing unit 450 and/or transmission of signals to internal component 444. As described below, in one embodiment, control module causes a control signal 475 to be transmitted to internal component 444.

In the embodiments illustrated in FIG. 4, internal component 444 comprises a stimulator/receiver unit 402, a stimulating assembly 418 and a pharmaceutical agent source 478. Stimulator/receiver unit 402 comprises a receiver module 458 that receives from transmitter 452 encoded data signals 472 and control signal 475. Stimulator/receiver unit 402 includes an electrical stimulation controller 460 that generates electrical stimulation signals 463 which are applied to the recipient via electrical contacts 430 of stimulating assembly 418. Electrical stimulation controller 460 generates electrical stimulation signals 463 based on encoded data signals 472 and cause perception of sound signal 403 by the recipient.

As noted, internal component comprises agent pharmaceutical agent source 478 which is fluidically coupled to agent delivery ports 420 in stimulating assembly 418. An agent released by pharmaceutical agent source 478 is applied to the nerve cells of the recipient's cochlea via agent delivery ports 420. Stimulator/receiver unit 402 includes a pharmaceutical agent controller 462 that controls the delivery of pharmaceutical agents to the recipient's cochlea. Specifically, pharmaceutical agent controller 462 comprises a port control module 474 to control ports 420 via, for example, electrical signals 465, and a source control module 476 to control the release of pharmaceutical agents from pharmaceutical agent source 478 to stimulating assembly 418. In the illustrative embodiment of FIG. 4, a coupling member, such as a catheter or tube 484, fluidically couples pharmaceutical agent source 478 to ports 420 in stimulating assembly 418.

As described below, in certain embodiments, pharmaceutical agent controller 462 causes a pharmaceutical agent to be applied based on control signal 475. In certain embodiments, stimulator/receiver unit 402 may cause concurrent application of the pharmaceutical agent and electrical stimulation signals 463.

As noted, in embodiments of the present invention, a pharmaceutical agent may be delivered to evoke a hearing percept of a received sound signal. In such embodiments, pharmaceutical agent controller 462 operates based on data signals 472. Furthermore, because the sound is perceived based on applied pharmaceutical agents, electrical stimulation controller 460 and electrical contacts 430 may be unnecessary.

Figure 5:
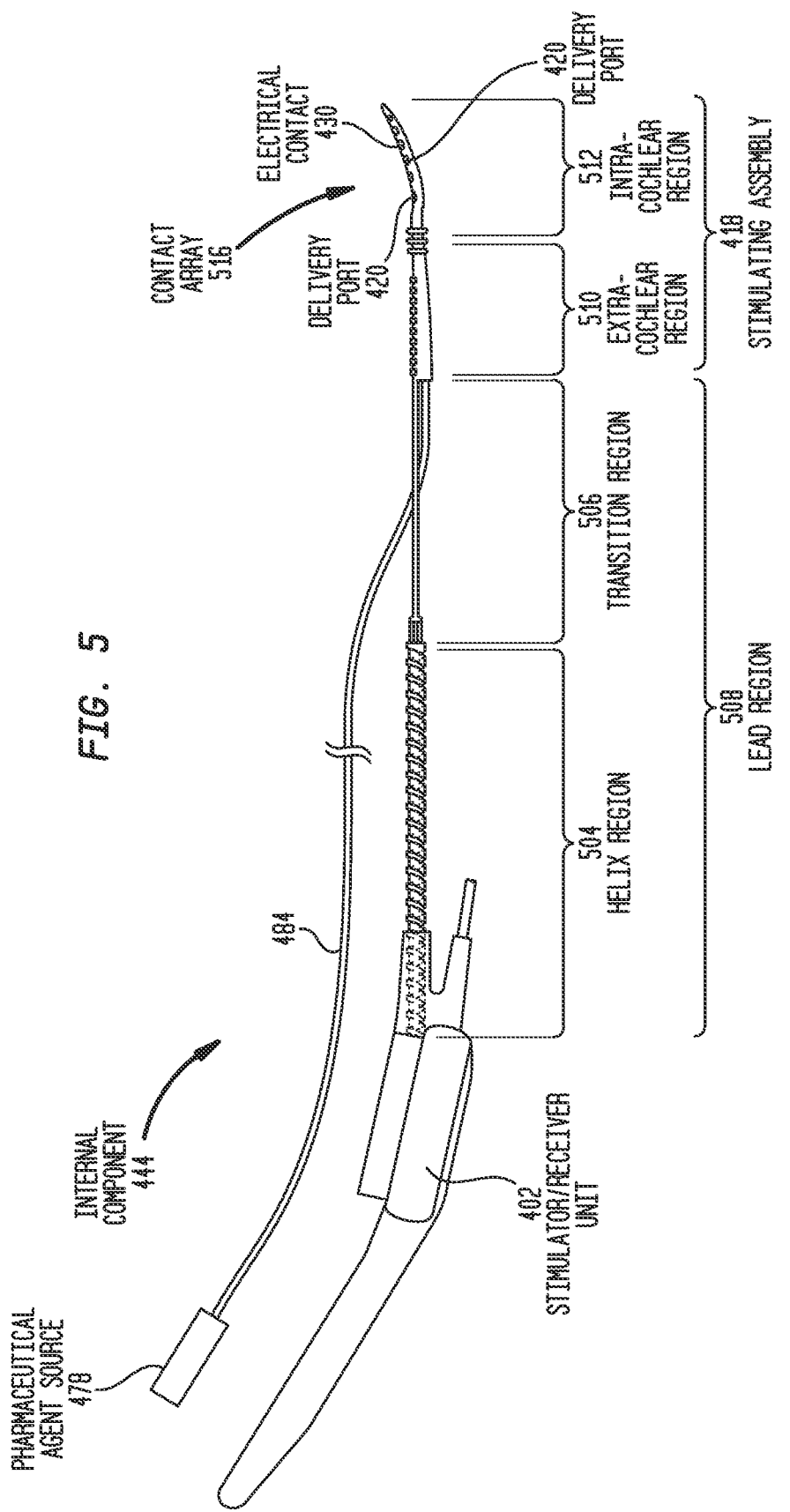
FIG. 5 is a side view of the implantable component of a cochlear implant in accordance with embodiments of the present invention.

FIG. 5 is a simplified side view of an embodiment of internal component 444. As noted, internal component 444 comprises a stimulator/receiver unit 402 which, as described above, receives encoded signals from an external component of the cochlear implant. Internal component 444 terminates in a stimulating assembly 418 that comprises an extra-cochlear region 510 and an intra-cochlear region 512. Intra-cochlear region 512 is configured to be implanted in the recipient's cochlea and has disposed thereon an array 516 of electrical contacts. Stimulating assembly 418 further includes one or more delivery ports 420.

In certain embodiments, stimulating assembly 418 is configured to adopt a curved configuration during and or after implantation into the recipient's cochlea. To achieve this, in certain embodiments, stimulating assembly 418 is pre-curved to the same general curvature of a recipient's cochlea. In such embodiments, of stimulating assembly 418 is sometimes referred to as perimodiolar stimulating assembly and is typically held straight by, for example, a stiffening stylet (not shown) which is removed during implantation so that the stimulating assembly may adopt its curved configuration when in the cochlea. Other methods of implantation, as well as other stimulating assemblies which adopt a curved configuration, may be used in alternative embodiments of the present invention.

In other embodiments, stimulating assembly 418 is a non-perimodiolar stimulating assembly which does not adopt a curved configuration. For example, stimulating assembly 418 may comprise a straight stimulating assembly or a mid-scala assembly which assumes a mid-scala position during or following implantation. In further embodiments, cochlear implant 400 could include a stimulating assembly implantable into a natural crevice in the cochlea that allows for the hydrodynamic nature of the cochlea to be maintained, or an assembly positioned adjacent to the cochlea.

Internal component 444 further comprises a lead region 508 coupling stimulator/receiver unit 402 to stimulating assembly 418. Lead region 508 comprises a helix region 504 and a transition region 506. Helix region 504 is a section of lead region 508 in which electrical leads are wound helically. Transition region 506 connects helix region 504 to stimulating assembly 418. Electrical stimulation signals generated by stimulator/receiver unit 402 are applied to contact array 516 via lead region 508. Helix region 504 prevents lead region 508, and thus the connection between stimulator/receiver 402 and stimulating assembly 418, from being damaged due to movement of internal component 444 which may occur, for example, during mastication.

As detailed above with reference to FIG. 4, stimulator/receiver unit 402 includes an electrical stimulation controller 460 (not shown) and a pharmaceutical agent controller 462 (also not shown). Pharmaceutical agent controller 462 controls the delivery of pharmaceutical agents from pharmaceutical agent source 478 to the cochlea. Specifically, agent controller 462 cause delivery of pharmaceutical agents to the cochlea in various temporal and spatial patterns and profiles, for example, by releasing a pharmaceutical agent in a continuous or pulsatile manner, and/or targeting areas of the cochlea. As described below, this delivery control is provided by controlling one or more of pharmaceutical agent source 478 and delivery ports 420.

In the embodiments of FIG. 5, pharmaceutical agent source 478 is physically separate from stimulator/receiver unit 402. Pharmaceutical agent source 478 is coupled to stimulating assembly 418 via a catheter or tube 484. For example, in embodiments of the present invention, pharmaceutical agent source 478 comprises a reservoir (not shown) for storing pharmaceutical agents. Pharmaceutical agent source 478 may be located underneath and proximate or adjacent to the recipient's skin so that the reservoir may be refilled when the agent therein is depleted. For example, the reservoir may include a post-operatively accessible refill port configured to receive a syringe therein. The syringe provides the pharmaceutical agent via an injection through the skin.

In certain embodiments of the present invention, pharmaceutical agent source 478 comprises an active infusion device. Such an active infusion device includes a pharmaceutical agent reservoir, a peristaltic pump to pump the agent from the reservoir, and a catheter port to connect pharmaceutical agent source 478 to a catheter. The catheter extends from agent source 478 to stimulating assembly 418. Pharmaceutical agent source 478 in accordance with such embodiments of the present invention may also include a battery to power the pump, an electronic module to control the flow rate of the pump, and possibly an antenna to permit the remote programming or control of the pump. It should be appreciated that agent source 478 may be secured internally or externally to the recipient.

In alternative embodiments of the present invention, pharmaceutical agent source 478 comprises a passive infusion device that does not include a pump. In such embodiments, pharmaceutical agent source 478 includes a pressurized reservoir that delivers the pharmaceutical agent to stimulating assembly 418 via a catheter. The pressurization of the reservoir is provided by a syringe capable of delivering pharmaceutical agents to the reservoir.

As detailed below, in alternative embodiments of the present invention, pharmaceutical agent source 478 may be integrated in stimulator/receiver unit 402 or stimulating assembly 418. In such embodiments, pharmaceutical agent source 478 comprises a reservoir within stimulating assembly 418. The reservoir may be connected to a post-operatively accessible refill element. The post-operatively accessible refill element may comprise an additional reservoir positioned underneath the skin as described above, or the refill element may comprise a refill port positioned underneath and proximate to the skin. In both cases, the refill element may be connected to the reservoir in stimulating assembly 418 via a catheter.

In embodiments of the present invention, delivery ports 420 are controllable to alter the flow rate through the ports. Such control may be provided by the implant, or externally, via, for example, electrical or mechanical signals, heat, etc.

Other systems and methods for delivering a pharmaceutical agent are within the scope of the present invention. For example, in one embodiment, a pharmaceutical agent is stored as a hydrogel rather than as a fluid within a reservoir.

As noted above, embodiments of the present invention are generally directed to a cochlear implant configured to apply combinations of electrical stimulation signals and pharmaceutical agents to a recipient's cochlea. As discussed in greater detail below, the cochlear implant is configured to control the timing, location, etc. of the delivery in order to cause a desired effect on a population of the recipient's cochlea nerve cells. FIG. 6 is a cross-sectional side view of a portion of an elongate stimulating assembly 618 which may be used in accordance with embodiments of the present invention to apply pharmaceutical agents and electrical stimulation signals to the recipient's cochlea. As noted above, elongate stimulating assembly 618 has a proximal end connected to a stimulator/receiver unit (not shown) and a distal end implantable in a recipient's cochlea. FIG. 6 illustrates a portion that is implantable into the cochlea.

Stimulating assembly 618 comprises a longitudinally aligned and distally extending array 646 of stimulating electrical contacts 630. Electrical contacts 630 receive electrical stimulation signals from the receiver/stimulator unit via one or more wires (not shown). The received electrical stimulation signals are then applied to the recipient's cochlea nerve cells. Stimulating assembly 618 further includes a plurality of pharmaceutical agent delivery ports 620 to apply agents to the cochlea. In this exemplary arrangement, delivery ports 620 include channels 622 which fluidically couple the ports to a pharmaceutical agent source, shown in FIG. 6 as agent reservoir 678 within stimulating assembly 618.

In certain embodiments, reservoir 678 may be coupled to an additional reservoir or refill element positioned outside of the cochlea. As noted, the stimulator/receiver unit includes one or more modules to control the operation of delivery ports 620, channel 622 and/or a pump (not shown) connected to reservoir 678 in order to control the delivery of the pharmaceutical agent to the recipient. For example, in one embodiment, the flow rate through delivery ports is electrically controllable. In other embodiments, channels 622 comprise controllable ion channels. FIGS. 8 and 9 illustrate exemplary arrangements for controlling a pharmaceutical agent source.

As noted above, a pharmaceutical agent may be applied to the recipient in accordance with embodiments of the present invention for a variety of purposes. For example, in one embodiment of the present invention, a pharmaceutical agent is applied to evoke stochastic or random activity within a nerve cell, referred to as pseudospontaneous nerve activity. This pseudospontaneous nerve activity replicates the spontaneous or random nerve activity experienced by individuals with normal hearing. By replicating the naturally occurring spontaneous activity cochlear implants may provide stimulated hearing that more closely replicates natural hearing. This may advantageously facilitate more accurate speech perceptions and/or the suppression of tinnitus.

In such embodiments of the present invention, a pharmaceutical agent is applied to the cochlea nerve cells in a desired temporal and spatial pattern to cause pseudospontaneous nerve activity in one or more regions of the cochlea. For example, in certain embodiments, the pharmaceutical agents are applied to evoke pseudospontaneous nerve activity in a specific region of the cochlea, a substantial portion of the cochlea, or in nerve cells adjacent specific electrical contacts. The pharmaceutical agent may be applied in a continuous or pulsatile manner. In certain embodiments, a BDNF is used to generate the pseudospontaneous nerve activity.

In embodiments of the present invention, the system is designed to control the level of pseudospontaneous nerve activity. That is, the cochlear implant may be designed such that the applied pharmaceutical agent causes a desired level of background random firing within the cochlea nerve cells. The level of pseudospontaneous nerve activity may be measured using, for example, neural response telemetry, and the system may adjust the delivery of the pharmaceutical agent (i.e. concentration, quantity, location, etc.) to obtain the desired level of random activity.

Also as noted above, electrical stimulation signals applied to a recipient's cochlea must have a minimum intensity in order to evoke a hearing percept. In other words, the electrical stimulation signals must have an intensity which increases the membrane voltage of the cells from the resting level (resting potential) to a level at which the nerve cells will fire. This level at which the nerve cells will fire is the recipient's auditory threshold level. Certain embodiments of the present invention apply to a population of cochlea nerve cells a pharmaceutical agent that reduces the recipient's auditory threshold level. Thus, electrical stimulation signals having a lower intensity will cause the nerve cells to fire.

In such embodiments, a threshold reducing pharmaceutical agent a brain derived neurotrophic factor (BDNF), ionic species, etc. is applied to the cochlea nerve cells in a desired temporal and spatial pattern. The pharmaceutical agent may be applied in a continuous or pulsatile manner. After the applied pharmaceutical agent reduces the firing threshold of the nerve cells, electrical stimulation signals generated based on a received sound signal are applied via electrical contacts. Due to the lower threshold of the nerve cells resulting from the pharmaceutical agent, the intensity of the electrical stimulation signals may be lower. This lower intensity results in the use of less power than is required in conventional cochlear implants. Furthermore, the lower intensity results in less spread of the electrical stimulation signals to nerve cells adjacent the stimulated cells. This reduced spread may provide for improved stimulation strategies which simultaneously or concurrently apply electrical stimulation signals via adjacent electrical contacts.

For example, in certain embodiments, the pharmaceutical agents are applied to reduce the firing threshold in a specific region of the cochlea, a substantial portion of the cochlea, or in nerve cells adjacent specific electrodes.

The firing threshold of a cochlear nerve cell depends on the concentration of ionic species at the cochlear nucleus, which is the first obligatory synapse in the ascending auditory path. In certain embodiments of the present invention, the firing threshold is lowered by delivering an ionic species to nerve cells adjacent or in proximity to one or more electrical contacts which are to apply electrical stimulation signals. In such embodiments, the pharmaceutical agent source contains an ionic species, and an ion channel terminating in a delivery port that applies the ionic species to the cochlea nerve cells adjacent to, or in close proximity to the delivery port. In other embodiments, a BDNF is used to lower firing threshold of the cochlea nerve cells.

In a further embodiment of the present invention, the cochlear implant is configured to apply pharmaceutical agents to the recipient's cochlea nerve cells to evoke a hearing percept of a received sound signal. In such embodiments, the pharmaceutical agent is applied under the control of a sound processor so that the recipient may perceive a sound signal received by the cochlear implant.

In such embodiments, the stimulating assembly comprises an array of delivery ports distributed along the length thereof. Similar to the arrangement of electrodes in conventional cochlear implants, the delivery ports are arranged on the assembly such that various regions of the tonotopically mapped cochlear are in proximity to the delivery ports. In other words, delivery ports are positioned adjacent nerve cells that are particularly sensitive to certain frequencies. Thus, a cochlear implant in accordance with embodiments of the present invention that uses pharmaceutical agents to evoke a hearing percept may be operated in a manner which is similar to conventional electrically stimulating cochlear implants. Specifically, sound signals within a certain frequency range are perceived by the recipient by delivering a pharmaceutical agent via delivery ports adjacent the nerve cells corresponding to the received frequency.

In embodiments of the present invention, the amount of pharmaceutical agent applied, as well as the concentration of the agent, may impact the response of the nerve cells to the pharmaceutical agent. Thus, the amount of agent released from different delivery ports 620 may be different depending on the desired application and the properties of the nerve cell population proximate to a delivery port.

Furthermore, in alternative embodiments of the present invention, the concentration of the pharmaceutical agent, or the agent itself, can differ between delivery ports 620. In such embodiments, the pharmaceutical agent source may be configured to deliver different agents or different concentrations of agents to different ports.

Figure 7A:
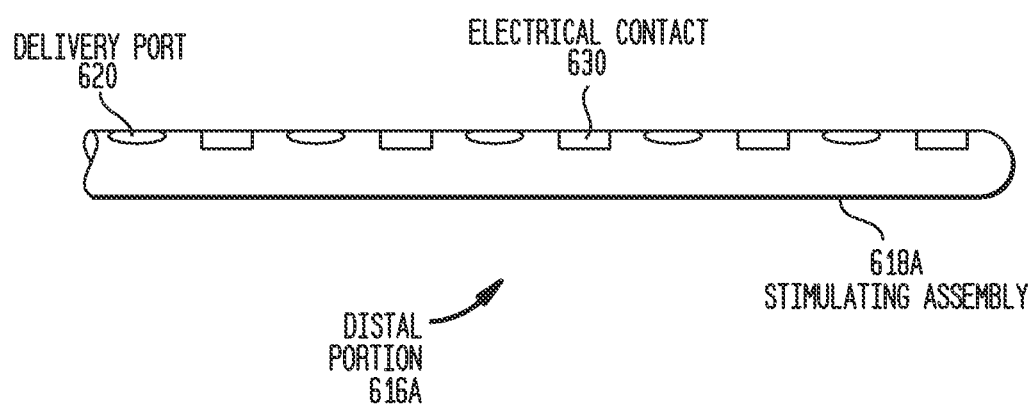
FIG. 7A is a side view of an implantable stimulating assembly in accordance with embodiments of the present invention.
Figure 7B:
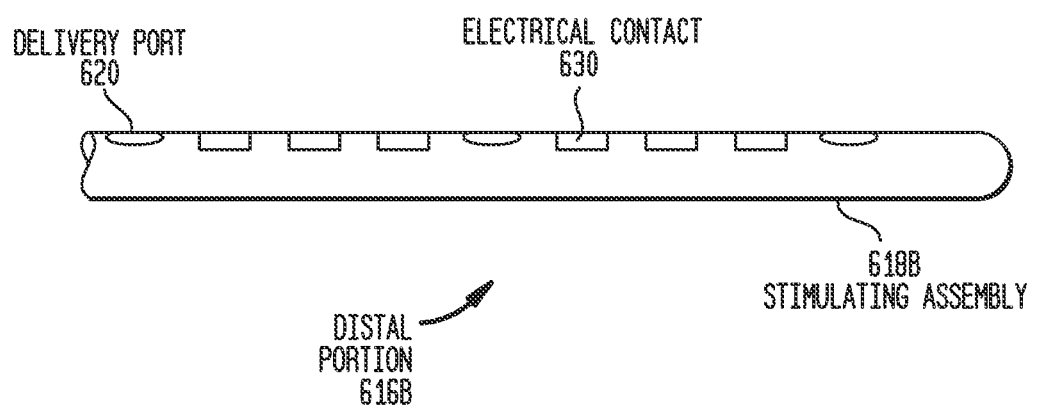
FIG. 7B is a side view of an implantable stimulating assembly in accordance with embodiments of the present invention.

FIG. 6 illustrates embodiments of the present invention in which delivery ports 620 are each disposed adjacent an electrical contact 630. It will be understood that the number and placement of the delivery ports 620 and electrical contacts 630 can be varied without departing from the scope of the present invention. FIGS. 7A and 7B are side views of stimulating assembly 618 illustrating alternative arrangements of delivery ports 620 and electrical contacts 630. For ease of illustration, electrical contacts 630 are depicted as rectangles and delivery ports 620 are depicted as ovals. These exemplary shapes are provided only to facilitate understanding of embodiments of the present invention and do not define or limit electrical contacts 630 or delivery ports 620 in any manner.

In FIG. 7A, a distal portion 616A of a stimulating assembly 618A is illustrated. As shown, electrical contacts 630 and delivery ports 620 are arranged in an alternating fashion. In other words, in the illustrated arrangement of FIG. 7A, no delivery ports 620 are adjacent other delivery ports. Similarly, no electrical contacts 630 are adjacent other electrical contacts. In contrast, as shown in FIG. 7B, a smaller number of delivery ports 620 are dispersed along distal portion 616B of stimulating assembly 618B.

FIG. 8 is a diagram illustrating a pharmaceutical agent source 802 for delivering pulses of a pharmaceutical agent to a recipient's cochlea in accordance with embodiments of the present invention. As shown, pharmaceutical agent source 802 comprises a reservoir 826 coupled to an outlet port, such as a delivery port 820. Disposed between reservoir 826 and delivery port 820 is an agent chamber 810 bound by two unidirectional valves 816. Agent chamber 810 is substantially filled with a pharmaceutical agent. In operation, pulses or cycles of electrical current are applied to opposing electrodes 806A and 806B (collectively, electrodes 806) in agent chamber 810 via heating element 812. Application of the electrical current to electrodes 806 results in the rapid heating and expansion of the agent within agent chamber 810 through, for example, thermal expansion and/or cavitation as the pharmaceutical agent near electrodes 806 boil. This expansion forces an amount of the agent in chamber 810 through unidirectional valve 816A towards delivery port 820. This is shown by arrow 821. Unidirectional valve 816B prevents the flow of the pharmaceutical agent towards reservoir 822. After the delivery of electrical current to electrodes 806 is stopped, the pharmaceutical agent within chamber 810 cools and contracts. This contraction draws additional agent from reservoir 826 through unidirectional valve 816B into chamber 810, shown by arrow 822.

As would be appreciated, the embodiments illustrated in FIG. 8 are used for pharmaceutical agents that do not experience property changes as the result of the application of heat thereto. If a heat sensitive pharmaceutical agent is used, the above described valve and chamber system may still be used, but heating element 812 is replaced with an electro-mechanical actuator which, when activated, is configured to change the physical volume of chamber 810. In such embodiments, the walls of agent chamber 810 are flexible so that the actuator contracts chamber 810 to force pharmaceutical agent out of unidirectional valve 816A, and expands chamber 810 to draw pharmaceutical agent in from reservoir 826. Suitable electro-mechanical actuators include piezoelectric devices, coil and magnet systems and electret devices. In both of the systems described with reference to FIG. 8, the amount of pharmaceutical agent applied to the cochlea can be controlled by controlling the amount and rate of the driving current applied to the chamber or actuator.

In the illustrative embodiment of FIG. 8, pharmaceutical agent source 802 is shown in close proximity to delivery port 820. It would be appreciated that source 802 is not necessarily close to delivery port 820. For example, a pharmaceutical agent released from valve 816A may be provided to a catheter connecting system 802 to delivery port 820.

Furthermore, in certain embodiments, a single pharmaceutical agent source 802 may be provided to deliver a pharmaceutical agent to multiple delivery ports 820. In alternative embodiments, multiple pharmaceutical agent sources 802 may be provided.

FIG. 9 is a diagram illustrating a pharmaceutical agent source 902 for delivering pulses of a pharmaceutical agent to a recipient's cochlea in accordance with embodiments of the present invention. As shown, pharmaceutical agent source 902 comprises an osmotic pump 940 to provide a pharmaceutical agent to a delivery port 920 via catheter 944.

As shown, osmotic pump 940 includes a housing 942 having a flexible reservoir 926 containing a pharmaceutical agent therein. A second portion of housing 942 comprises an ionic chamber 946 that contains a fluid having a lower ionic concentration that fluid external to housing 942. An osmotic membrane 950 forms a part of housing 942 which separates ionic chamber 946 from the external fluid. Osmotic pump 940 relies upon an osmotic pressure difference between the ionic chamber 946 and the external fluid to release the pharmaceutical agent from reservoir 946. Specifically, the osmotic pressure difference causes water to flow into the pump through the semi-permeable osmotic membrane 950. As the water enters ionic chamber 946, ionic chamber 946 exerts a force 952 that compresses flexible reservoir 926, thereby displacing the pharmaceutical agent from reservoir 926.

In the illustrative embodiment of FIG. 9, pharmaceutical agent source 902 is shown in close proximity to delivery port 920. It would be appreciated that source 902 is not necessarily close to delivery port 920. Furthermore, in certain embodiments, a single pharmaceutical agent source 902 may be provided to deliver a pharmaceutical agent to multiple delivery ports 920. In alternative embodiments, multiple pharmaceutical agent sources 902 may be provided.

As detailed above, electrical stimulation signals applied to a recipient's cochlea must have a minimum intensity in order to evoke a hearing percept. In other words, the electrical stimulation signals must have an intensity which increases the membrane voltage of the cells from the resting level (resting potential) to a level at which the nerve cells will fire. This level at which the nerve cells will fire is the recipient's auditory threshold level. Certain embodiments of the present invention apply to a population of cochlea nerve cells a pharmaceutical agent that reduces the recipient's auditory threshold level. Thus, electrical stimulation signals having a lower intensity will cause the nerve cells to fire.

In such embodiments, a threshold reducing pharmaceutical agent a brain derived neurotrophic factor (BDNF), ionic species, etc. is applied to the cochlea nerve cells in a desired temporal and spatial pattern. The pharmaceutical agent may be applied in a continuous or pulsatile manner. After the applied pharmaceutical agent reduces the firing threshold of the nerve cells, electrical stimulation signals generated based on a received sound signal are applied via electrical contacts. Due to the lower threshold of the nerve cells resulting from the pharmaceutical agent, the intensity of the electrical stimulation signals may be lower. This lower intensity results in the use of less power than is required in conventional cochlear implants. Furthermore, the lower intensity results in less spread of the electrical stimulation signals to nerve cells adjacent the stimulated cells. This reduced spread may provide for improved stimulation strategies which simultaneously apply electrical stimulation signals via adjacent electrical contacts.

Figure 10A:
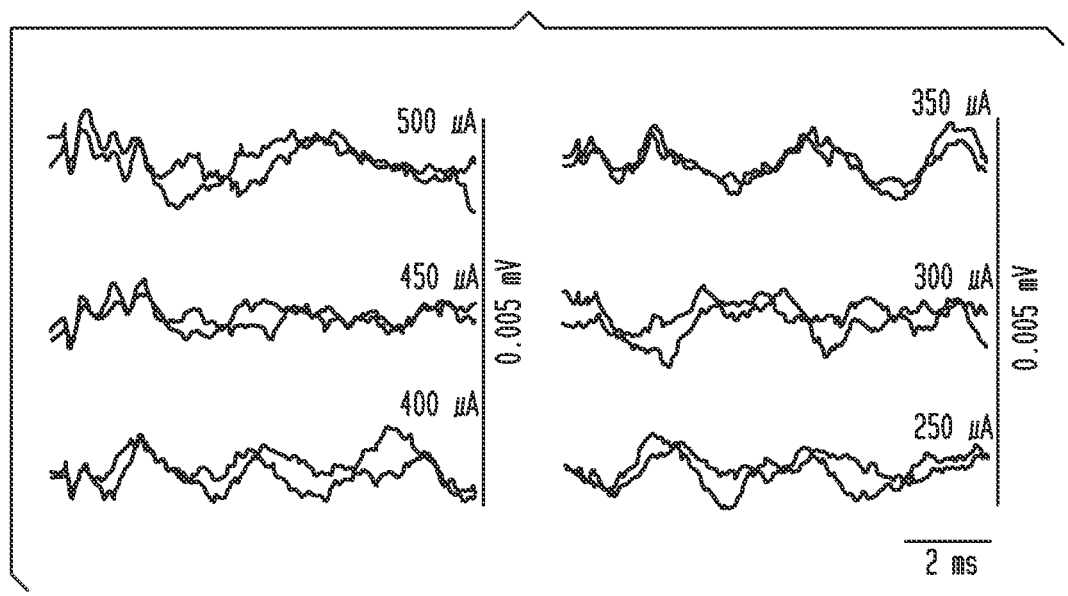
FIG. 10A illustrate the responses of a recipient's cochlear prior to, and following, the delivery of a pharmaceutical agent to the cochlea.
Figure 10B:
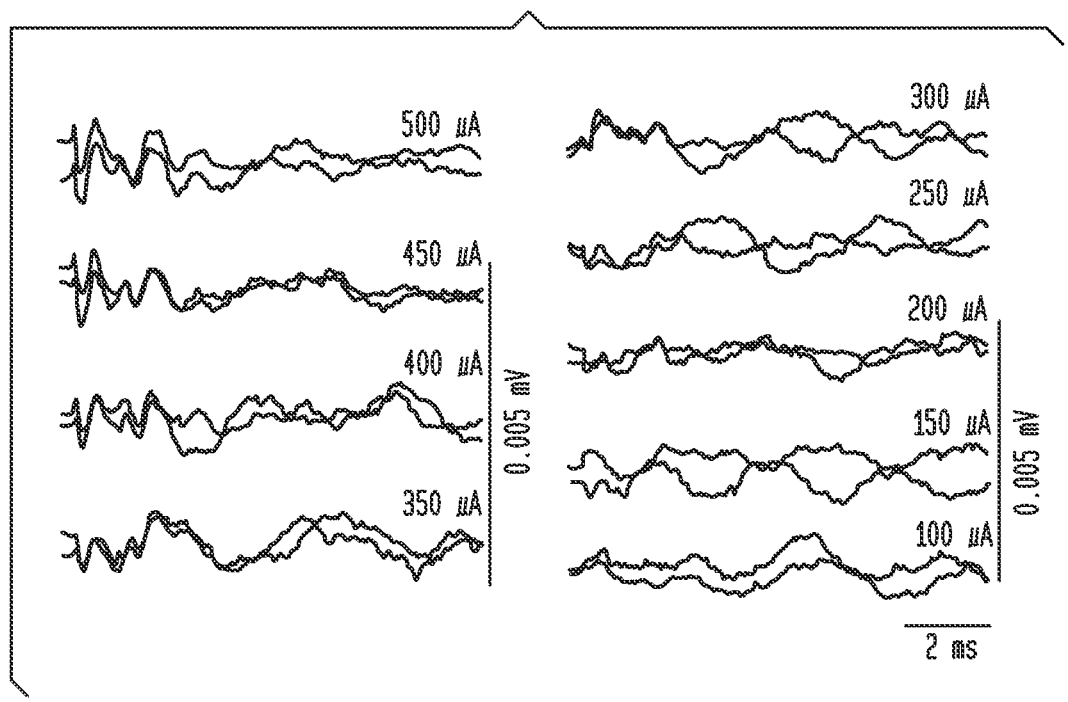
FIG. 10B illustrate the responses of a recipient's cochlear prior to, and following, the delivery of a pharmaceutical agent to the cochlea.

FIGS. 10A and 10B illustrate embodiments of the present invention in which pharmaceutical agents are applied to reduce the firing threshold of nerve cells. Specifically, the left-side graphs of FIGS. 10A and 10B illustrate the current required to evoke a hearing percept of a sound signal at different regions of the cochlear prior to delivery of a threshold reducing pharmaceutical agent to the cochlea nerve cells. The right-side graphs of FIGS. 10A and 10B illustrate the reduced current required to evoke a hearing percept of a sound signal at the regions of the cochlear following delivery of a threshold reducing pharmaceutical agent to the cochlea nerve cells.

FIG. 11 is a flowchart illustrating the operations performed by a cochlear implant in accordance with embodiments of the present invention to lower a recipient's threshold as described above with reference to FIGS. 10A and 10B. The method begins at block 1102. At block 1104, a sound signal is received by the cochlear implant. At block 1106, a threshold reducing pharmaceutical agent is applied to a recipient's cochlea 140 (FIG. 1). At block 1108, electrical stimulation signals are generated based on the received sound signal, and are applied to cochlea 140. As described above, these electrical stimulation signals have an intensity which is lower than that required to evoke a hearing percept in conventional cochlear implants. The method then ends at block 1110. As would be appreciated by one of ordinary skill in the art, the operations of blocks 1106 and 1108 may occur concurrently, with appropriate delays for generation and/or application of electrical stimulation signals so that the membrane voltage of the nerve cells increases to the critical threshold.

Figure 12A:
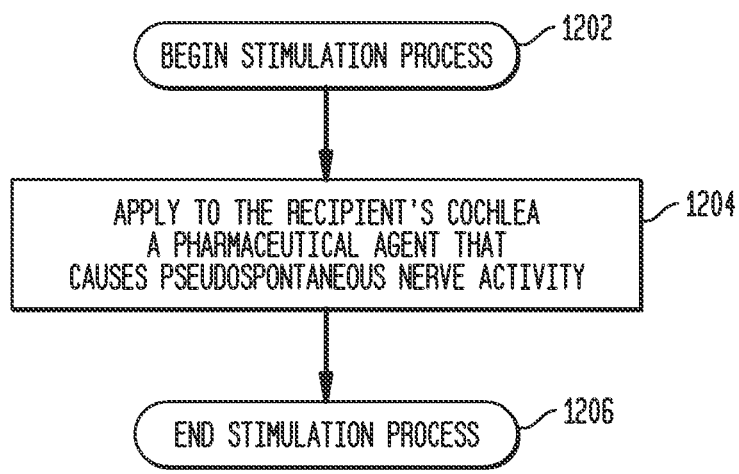
FIG. 12A is a flowchart illustrating the operations performed by a cochlear implant in accordance with embodiments of the present invention.

As described above, in certain embodiments of the present invention, a pharmaceutical agent may be applied to the recipient to evoke pseudospontaneous nerve activity. This pseudospontaneous nerve activity replicates the spontaneous or random nerve activity experienced by individuals with normal hearing. In such embodiments of the present invention, a pharmaceutical agent is applied to the cochlea nerve cells in a desired temporal and spatial pattern to cause pseudospontaneous nerve activity in one or more regions of the cochlea. FIG. 12A is a high level flowchart illustrating the operations performed by a cochlear implant in accordance with such embodiments of the present invention. The stimulation process begins at block 1202. At block 1204, a pharmaceutical agent is applied to one or more regions of the recipient's nerve cells to encourage, facilitate or allow pseudospontaneous nerve activity. The stimulation process then ends at block 1206.

FIG. 12B is a detailed flowchart illustrating the operations that may be performed in accordance with embodiments of block 1204 of FIG. 12A. The operations begin at block 1210. At block 1212, a decision is made if a sound signal has been received and/or whether the signal should be processed. If a received sound signal is to be processed, the method progresses to blocks 1214 and 1215. At block 1215, a pharmaceutical agent is applied to the recipient's nerve cells to encourage, facilitate or allow pseudospontaneous nerve activity. At block 1214, electrical stimulation signals based on the received sound signal are generated and applied to the recipient's nerve cells. The operations of blocks 1215 and 1214 may occur sequentially or concurrently. The operations then end at block 1222.

Returning to block 1212, if no sound signal is to be processed, the method progresses to block 1218. A block 1218 a determination is made as to whether pseudospontaneous auditory nerve activity is desired. If pseudospontaneous auditory nerve activity is not desired, the method ends at block 1222. However, if pseudospontaneous auditory nerve activity is desired, the method continues to block 1220. At block 1220, a pharmaceutical agent is applied to the recipient's nerve cells to encourage, facilitate or allow pseudospontaneous nerve activity. The method then ends at block 1222.

In a further embodiment of the present invention, the cochlear implant is configured to apply pharmaceutical agents to the recipient's cochlea to evoke a hearing percept of a received sound signal. The pharmaceutical agent is applied under the control of a sound processor so that the recipient may perceive a sound signal received by the cochlear implant. In certain such embodiments, the cochlea does not require the ability to electrically stimulate the cochlea.

In such embodiments, the stimulating assembly comprises an array of delivery ports distributed along the length thereof. Similar to the arrangement of electrodes in conventional cochlear implants, the delivery ports are arranged on the assembly such that various regions of the tonotopically mapped cochlear are in proximity to the delivery ports. In other words, delivery ports are positioned adjacent nerve cells that are particularly sensitive to certain frequencies. Thus, a cochlear implant in accordance with embodiments of the present invention that uses pharmaceutical agents to evoke a hearing percept may be operated in a manner which is similar to conventional electrically stimulating cochlear implants. Specifically, sound signals within a certain frequency range are perceived by the recipient by delivering a pharmaceutical agent via delivery ports adjacent the nerve cells corresponding to the received frequency.

Figure 13:
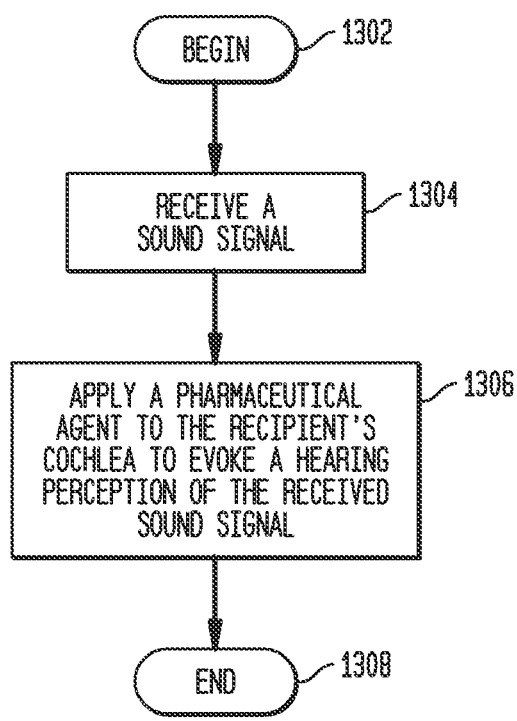
FIG. 13 is a flowchart illustrating the operations performed by a cochlear implant in accordance with embodiments of the present invention.

FIG. 13 is a flowchart illustrating the operations performed by a cochlear implant in accordance with such embodiments of the present invention. The method begins at block 1302. At block 1304, a sound signal is received by the implant. At block 1306, the cochlear implant delivers a pharmaceutical agent to the recipient's cochlea. The pharmaceutical agent is applied to evoke a hearing perception of the received sound signal. The method then ends at block 1308.

Although embodiments of the present invention have been primarily described with reference to a cochlear implant, it should be appreciated that alternative embodiments may be implanted in a variety of stimulating medical devices or prosthetic hearing devices such as acoustic hearing aids, middle ear implants, brain stem implants, or any combination of these, or other implanted devices. For example, embodiments may be implemented in a device implantable in the cochlear nucleus, the superior olive, the nucleus of the lateral lemniscus, the inferior colliculus, the medial geniculate body, the auditory cortex, Subthalamic Nucleus (STN), the Globus Pallidus (GPi), and/or the Thalamus.

All documents, patents, journal articles and other materials cited in the present application are hereby incorporated by reference.

Although the present invention has been fully described in conjunction with several embodiments thereof with reference to the accompanying drawings, it is to be understood that various changes and modifications may be apparent to those skilled in the art. Such changes and modifications are to be understood as included within the scope of the present invention as defined by the appended claims, unless they depart there from.

What is claimed is:

1. A method for stimulating a cochlea of a recipient with a cochlear implant comprising a stimulating assembly implantable in the cochlea and having at least one agent delivery port and a plurality of electrical contacts, the method comprising:
    applying electrical stimulation signals to a first population of nerve cells in the cochlea via one or more of the plurality of electrical contacts;
    applying a pharmaceutical agent to a second population of nerve cells in the cochlea via the at least one delivery port to invoke pseudospontaneous activity in the second population of nerve cells such that the combination of the pseudospontaneous activity and spontaneous activity in the second population of nerve cells results in a total stochastic nerve activity which is greater that the spontaneous nerve activity and which is below the recipient's auditory threshold; and
    applying, concurrent with the application of the pharmaceutical agent, electrical stimulation signals to the second population of nerve cells via one or more of the plurality of electrical contacts.

2. The method of claim 1, wherein the pharmaceutical agent is a brain derived neurotrophic factor.

3. The method of claim 1, wherein the pseudospontaneous activity in the second population of cochlea nerve cells of the recipient is below an auditory threshold of the recipient.

4. The method of claim 1, wherein applying the pharmaceutical agent to the second population of cochlea nerve cells comprises applying the pharmaceutical agent in a desired temporal and spatial pattern.

5. The method of claim 4, further comprising applying the pharmaceutical agent to the second population of cochlea nerve cells in a continuous manner.

6. The method of claim 4, further comprising applying the pharmaceutical agent to the second population of cochlea nerve cells in a pulsatile manner.

7. The method of claim 1, further comprising measuring the stochastic activity in the second population of nerve cells.

8. The method of claim 7, further comprising measuring the stochastic activity in the second population of nerve cells using neural response telemetry.

9. The method of claim 1, further comprising:
    adjusting the application of the pharmaceutical agent based on a measurement of the stochastic activity and the desired level of the pseudospontaneous activity.

10. The method of claim 1, wherein applying the pharmaceutical agent to the second population of cochlea nerve cells comprises:
    controlling the release of pharmaceutical agents from the at least one agent delivery port.

11. The method of claim 10, wherein controlling the release of the pharmaceutical agents comprises controlling the concentration of the pharmaceutical agents released from the at least one delivery port.

* * * * *